(12) United States Patent
Rothermel

(10) Patent No.: US 9,687,620 B2
(45) Date of Patent: Jun. 27, 2017

(54) PATIENT INTERFACE WITH SNAP-FIT CONNECTOR

(71) Applicant: KONINKLIJKE PHILIPS N.V., Eindhoven (NL)

(72) Inventor: Justin Edward Rothermel, Monroeville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 333 days.

(21) Appl. No.: 14/356,255

(22) PCT Filed: Nov. 6, 2012

(86) PCT No.: PCT/IB2012/056175
§ 371 (c)(1),
(2) Date: May 5, 2014

(87) PCT Pub. No.: WO2013/068911
PCT Pub. Date: May 16, 2013

(65) Prior Publication Data
US 2014/0305433 A1    Oct. 16, 2014

Related U.S. Application Data

(60) Provisional application No. 61/556,320, filed on Nov. 7, 2011.

(51) Int. Cl.
*A61M 16/06* (2006.01)
*A61M 16/00* (2006.01)
*A61M 16/08* (2006.01)

(52) U.S. Cl.
CPC ........ *A61M 16/0057* (2013.01); *A61M 16/06* (2013.01); *A61M 16/0622* (2014.02);
(Continued)

(58) Field of Classification Search
CPC .............. A61M 16/00; A61M 16/0066; A61M 16/009; A61M 16/0093; A61M 16/06;
(Continued)

(56) References Cited

U.S. PATENT DOCUMENTS 5,577,693 A * 11/1996 Corn .................. A61M 16/009
                                                              128/910
5,676,133 A * 10/1997 Hickle .................. A61M 16/00
                                                              128/202.27
(Continued)

FOREIGN PATENT DOCUMENTS

AU   WO 2010135785 A1 * 12/2010 ............ A61M 16/06
CN          2635116 Y        8/2004
(Continued)

*Primary Examiner* — Annette Dixon
(74) *Attorney, Agent, or Firm* — Michael W. Haas

(57) ABSTRACT

A connector (36) is employed in a patient interface (2) that provides a flow of breathable gas to an airway of a patient. The connector includes a support apparatus (48) and a connection apparatus (50). The support apparatus is connected with a source of a breathable gas (4). The connection apparatus is disposed on the support apparatus and is engaged with the cushion. The connection apparatus includes an engagement element (78) and a retention apparatus (80). The engagement element has a frusto-conic engagement surface (84) that is structured to receive against it at least a portion of the cushion. The retention apparatus includes at least a first retention element (86) engaged with the cushion and retaining the at least portion of the cushion in a condition received against the engagement surface.

13 Claims, 5 Drawing Sheets

(52) U.S. Cl.
CPC .... *A61M 16/0683* (2013.01); *A61M 16/0816* (2013.01); *A61M 16/0616* (2014.02); *A61M 16/0633* (2014.02)

(58) Field of Classification Search
CPC .......... A61M 16/0611; A61M 16/0616; A61M 16/0622; A61M 16/0633; A61M 16/0644; A61M 16/0666; A61M 16/0683; A61M 16/0688; A61M 16/0816; A61M 16/0825; A61M 2205/42; A61M 2210/0618; Y02C 20/10
USPC ............ 128/202.27, 203.29, 204.18, 205.12, 128/205.24, 205.25, 206.15, 206.21, 128/206.22, 206.24, 206.25, 206.26, 128/206.27, 206.28, 207.11, 207.18, 910, 128/912, 916
See application file for complete search history.

(56) References Cited

U.S. PATENT DOCUMENTS

| | | | |
|---|---|---|---|
| 6,467,483 | B1 | 10/2002 | Kopacko |
| 6,491,034 | B1 * | 12/2002 | Gunaratnam ......... A61M 16/06 128/202.27 |
| 8,342,181 | B2 * | 1/2013 | Selvarajan ............ A61M 16/06 128/206.21 |
| 2003/0196662 | A1 | 10/2003 | Ging |
| 2004/0112385 | A1 | 6/2004 | Drew |
| 2006/0005840 | A1 * | 1/2006 | Cannon ............. A61M 16/0683 128/207.11 |
| 2007/0277828 | A1 | 12/2007 | Ho |
| 2008/0314388 | A1 * | 12/2008 | Brambilla ............. A61M 16/06 128/205.25 |
| 2009/0223521 | A1 | 9/2009 | Howard |
| 2010/0236549 | A1 | 9/2010 | Selvarajan |
| 2010/0319700 | A1 | 12/2010 | Ng |

FOREIGN PATENT DOCUMENTS

| | | |
|---|---|---|
| CN | 1784250 A | 6/2006 |
| CN | 101543656 A * | 9/2009 |
| CN | 101543656 A | 9/2009 |
| DE | 29721766 U1 | 2/1998 |
| EP | 2741666 A1 | 6/2014 |
| EP | 2741802 A1 | 6/2014 |
| WO | WO2004096332 A1 | 11/2004 |
| WO | WO2005097247 A1 | 10/2005 |
| WO | WO2013021172 A1 | 2/2013 |
| WO | WO2013022356 A1 | 2/2013 |

* cited by examiner

PATIENT INTERFACE WITH SNAP-FIT CONNECTOR

CROSS-REFERENCE TO RELATED APPLICATIONS

This patent application claims the priority benefit under 35 U.S.C. §371 of international patent application no. PCT/IB2012/056175, filed Nov. 6, 2012, which claims the priority benefit under 35 U.S.C. §119(e) of U.S. Provisional Application No. 61/556,320 filed on Nov. 7, 2011, the contents of which are herein incorporated by reference.

BACKGROUND OF THE INVENTION

1. Field of the Invention

The present invention pertains to a patient interface for delivering a flow of breathable gas to a patient and, in particular, to an improved connector of an improved patient interface that is movably connected to a cushion and a frame of the patient interface.

2. Description of the Related Art

There are numerous situations where it is necessary or desirable to deliver a flow of breathable gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a respiratory patient interface device including a patient interface that is typically secured on the face of a patient by a headgear assembly. The patient interface may be, without limitation, a nasal mask that covers the patient's nose, a nasal cushion having nasal prongs that are received within the patient's nares, a nasal/oral mask that covers the nose and mouth, or full face mask that covers the patient's face. It is known to maintain such devices on the face of a wearer by a headgear having one or more straps adapted to fit over/around the patient's head. Because such respiratory patient interface devices are typically worn for an extended period of time, it is important for the headgear to maintain the patient interface in a desired position while doing so in a manner that is comfortable to the patient.

It is also desirable, however, that the respiratory patient interface device be relatively easy for the patient to maintain. For example, the nasal mask or nasal cushion or nasal/oral mask typically must periodically be cleaned by the patient. Previous devices that have been comfortable for the patient for extended periods and that maintain a reliable seal on the patient's face for extended periods have typically been relatively complicated devices that have been somewhat difficult to disassemble for cleaning purposes. On the other hand, previous device that have been relatively simple for the patient to disassemble and assemble have had seals that have been somewhat less than completely reliable. It thus would be desirable to provide an improved patient interface.

SUMMARY OF THE INVENTION

In certain embodiments, the general nature of the invention can be stated as including an improved connector structured to be employed in a patient interface wherein the patient interface is structured to provide a flow of breathable gas to an airway of a patient. The patient interface has a resilient cushion that is structured to be engaged with the face of the patient. The connector can be generally stated as including a support apparatus and a connection apparatus. The support apparatus is structured to be connected with a source of breathable gas. The connection apparatus is disposed on the support apparatus and is structured to be engaged with the cushion. The connection apparatus can be generally stated as including an engagement element and a retention apparatus. The engagement element has a frusto-conic engagement surface that is structured to receive against it at least a portion of the cushion. The retention apparatus can be generally stated as including at least a first retention element that is structured to be engaged with the cushion and to retain the at least portion of the cushion in a condition received against the engagement surface.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENT

Figure 1:
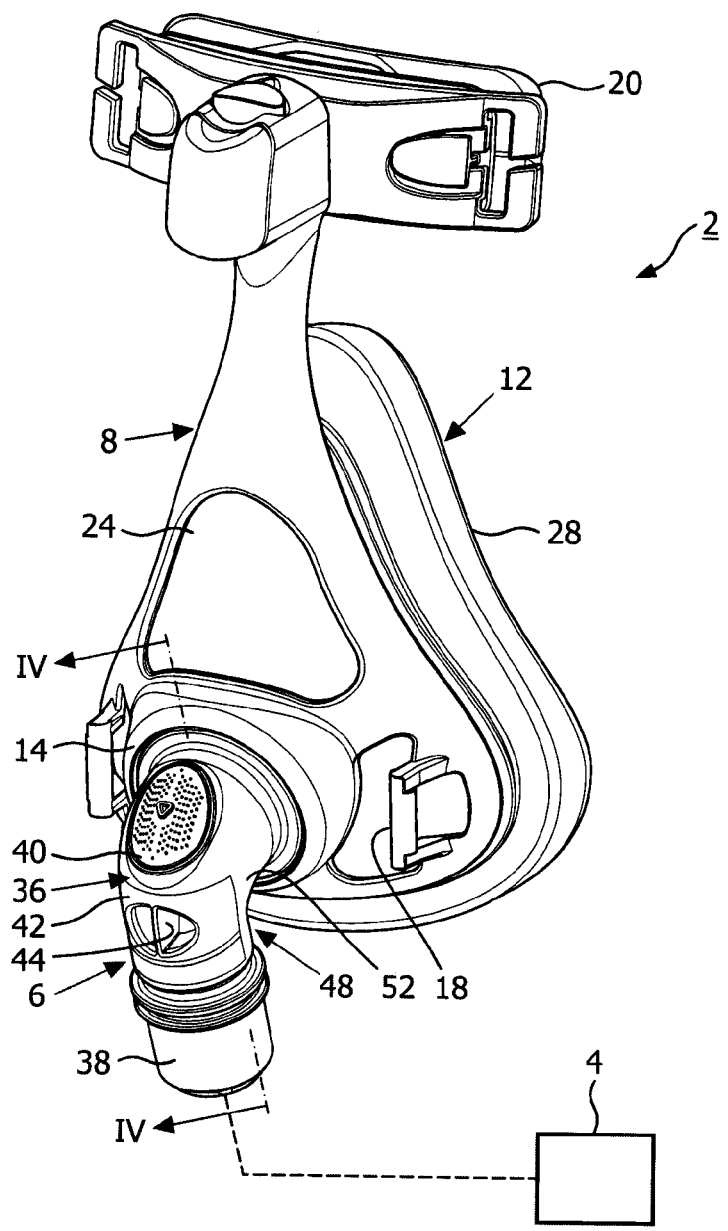
FIG. 1 is a front elevational view of an improved patient interface in accordance with the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2:
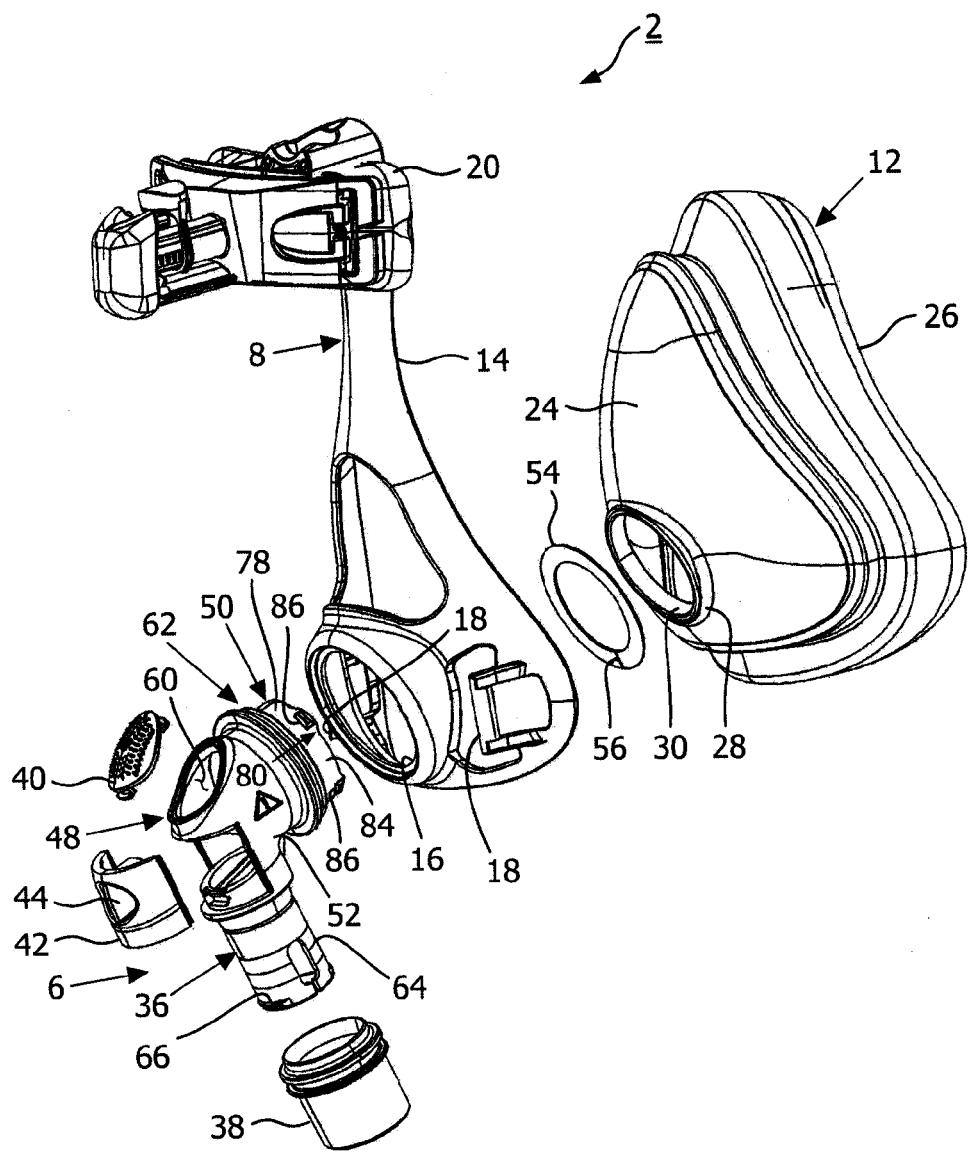
FIG. 2 is an exploded view of the patient interface of FIG. 1.

An improved patient interface 2 in accordance with an exemplary embodiment of the invention is depicted generally in FIGS. 1 and 2. In FIG. 2, patient interface 2 is depicted in an exploded condition. Patient interface 2 is advantageously configured to provide a flow of breathable gas to the airways of a patient that is not expressly depicted herein for purposes of simplicity of disclosure.

Patient interface 2 can be said to be connected with a source of breathable gas 4, such as may include a CPAP machine or other appropriate device. Patient interface 2 is in fluid communication with source of breathable gas 4 via a hose that is not expressly depicted herein for purposes of simplicity of disclosure. The breathable gas that is provided to patient interface 2 can be any of a wide variety of gases including combinations of gases such as air or other combinations of gases.

Patient interface 2 can be said to include a supply apparatus 6 that is in fluid communication with source of breathable gas 4. Patient interface 2 further includes a headgear 8 and a cushion 12 that are both mounted on a portion of supply apparatus 6, as will be set forth in greater detail below.

Headgear 8 can be said to include a frame 14 having an opening 16 formed therein. Opening 16 is, in the depicted exemplary embodiment, substantially circular in shape for reasons that will be set forth in greater elsewhere herein. Frame 14 further includes a pair of posts 18 to which can be connected a strap that is used to mount headgear 8 and patient interface 2 on the patient. The strap is not depicted herein for purposes of simplicity of disclosure. Headgear 8 can further be said to include a forehead brace 20 that is mounted on frame 14 and that is engageable with a forehead of the patient. Another strap is connectable with frame 14 in the vicinity of forehead brace 20 to connect headgear 8 with the patient, it being understood that such a strap is likewise not depicted herein for purposes of simplicity of disclosure.

As can be best understood from FIG. 2, cushion 12 can be said to include a cushion base 24 and a cushion element 26 that are connected together. Cushion base 24 may be formed of a first resilient material such as a hard thermoplastic material or other material, and cushion element 26 can be formed of a second, different material such as a soft and pliable silicone material that results, for example, from a liquid silicone resin being formed to and cured against cushion base 24. It is noted, however, that other materials can be employed for cushion base 24 and cushion element 26 as needed. It is also expressly noted that cushion 12 can be a unitary element wherein cushion base 24 and cushion element 26 are together formed as a single element out of the same material. Other variations will be apparent.

Figure 4:
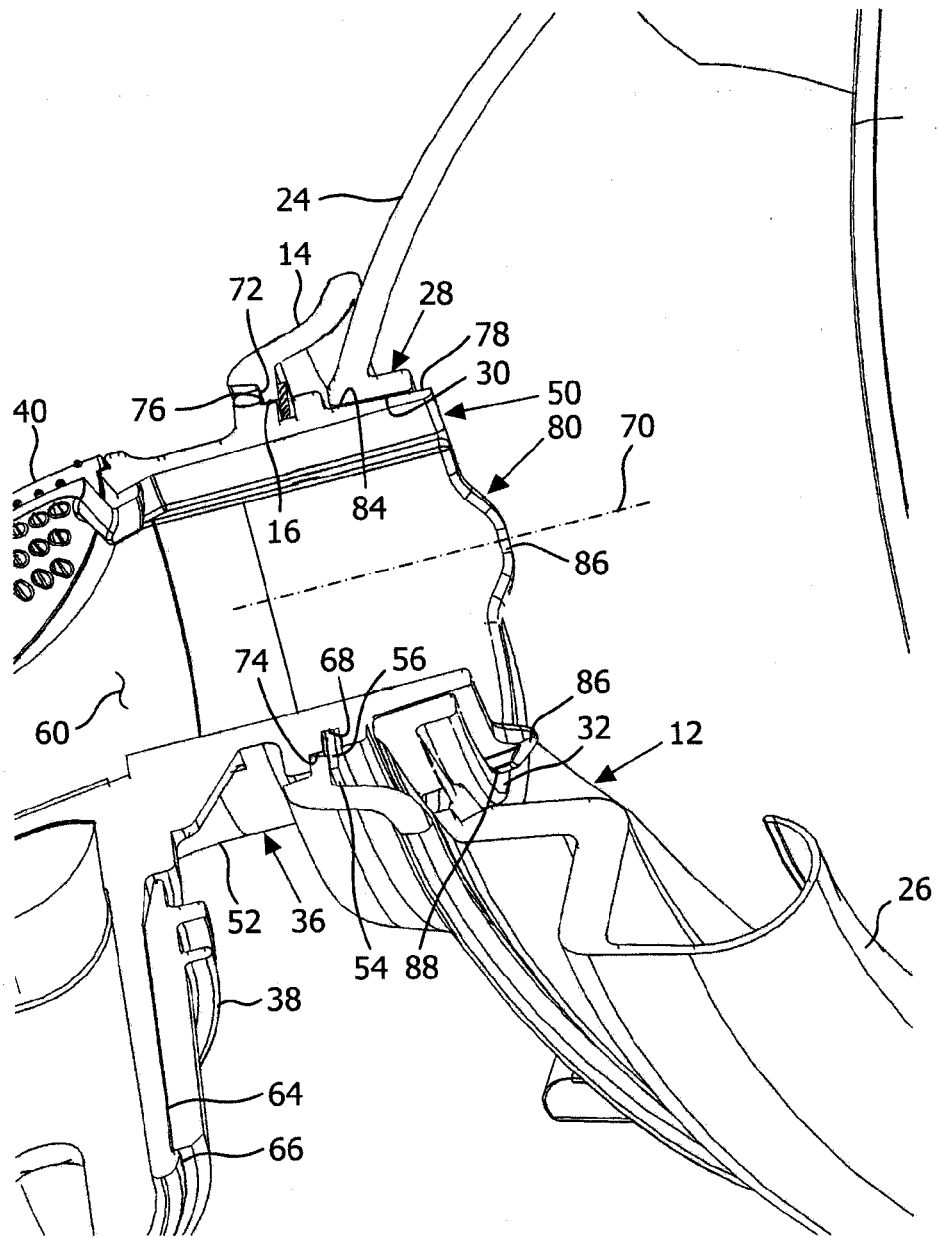
FIG. 4 is a sectional view as taken along line 4-4 of FIG. 1.

Cushion element 26 can be understood to be receivable against the face of the patient. Opposite cushion element 26, cushion base 24 includes a seal element 28 that is structured to be sealingly received against supply apparatus 6 in a fashion that will be set forth in greater detail below. Seal element 28 includes a seal surface 30 that is depicted in FIG. 2 and which, as will be described in greater detail below, is of a substantially frusto-conic shape. Seal element 28 also includes an annular abutment surface 32 that is depicted in FIG. 4 and will be discussed elsewhere herein.

As can be understood from FIG. 2, supply apparatus 6 can be said to include a connector 36, a swivel element 38, an exhalation plate 40, and a closure 42. Exhalation plate 40 is mounted to connector 36 and has a plurality of holes formed therein through which exhaled gases can flow in a well-known manner. Closure 42 is likewise mountable on connector 36 and has an atmospheric port 44 formed therein to allow the patient to inhale if source of breathable gases 4 should fail for whatever reason. Swivel element 38 is rotatably received on connector 36 and permits connector 36 and the tube that extends between supply apparatus 6 and source of breathable gases 4 to be pivotable with respect to one another.

Figure 3:
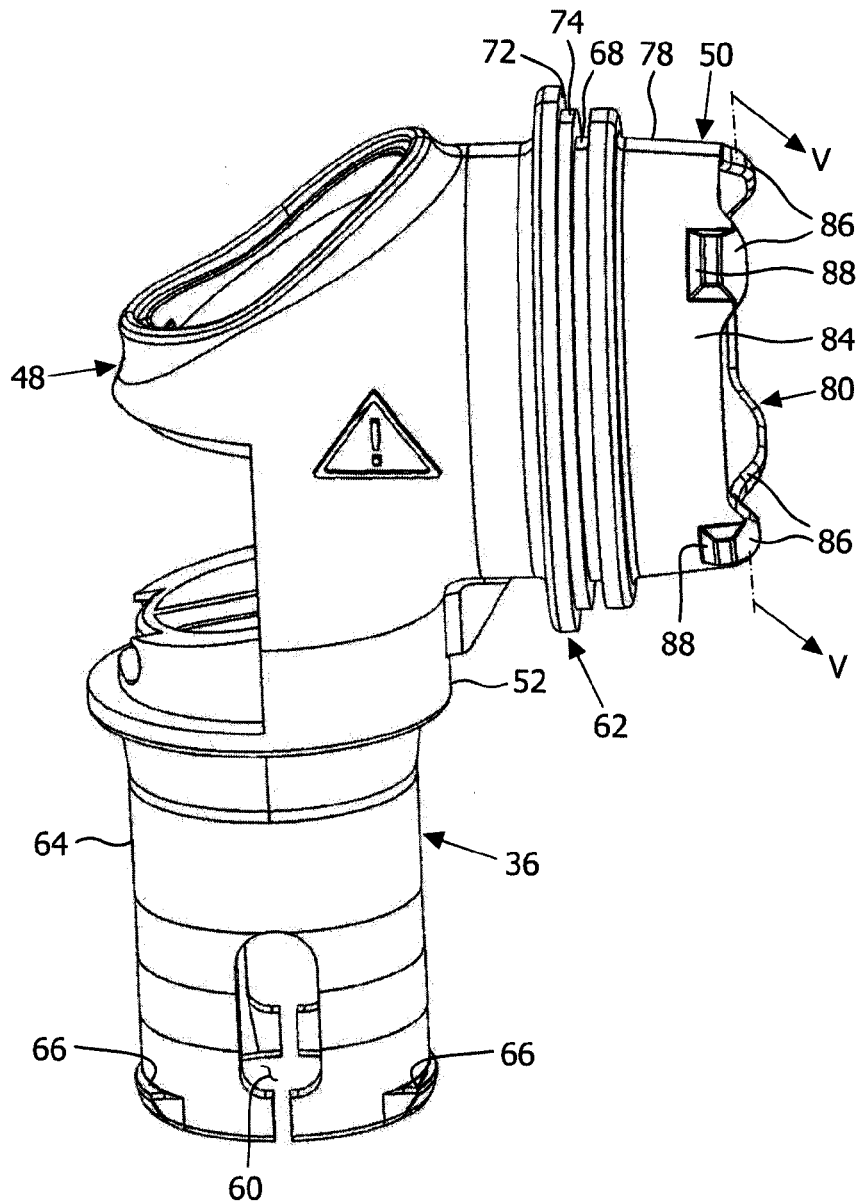
FIG. 3 is an enlarged view of a portion of the patient interface of FIGS. 1 and 2.

As can be best understood from FIG. 3, connector 36 can be said to include a support apparatus 48 and a connection apparatus 50 that are connected together. As will be set forth in greater detail below, cushion 12 is mountable to connection apparatus 50, and frame 14 is mountable to support apparatus 48. As such, cushion 12 and headgear 8 are both mounted to connector 36. Moreover, and as will likewise be set forth in greater detail below, headgear 8 and cushion 12 are both actually movably mounted to connector 36. That is, connector 36 is pivotable with respect to headgear 8 and cushion 12. Since connector 36 is also pivotable with respect to swivel element 38 and the tube that connects swivel element 38 with source of breathable gas 4, the movability of connector 36 with the other elements to which it is connected promotes a high degree of comfort to the patient during use of patient interface 2.

Support apparatus 48 can be said to include a support element 52, a mounting apparatus 62, and a swivel base 64. A flow passage 60 is formed within support apparatus 48 and carried the flow of breathable gases from source of breathable gases 4 to cushion 12. Support element 52 is generally elbow-shaped and has mounting apparatus 62 disposed at one end thereof and has swivel base 64 disposed at another end thereof. Swivel base 64 includes a plurality of latches 66 that pivotably retain swivel element movably disposed on swivel base 64.

Support apparatus 48 can be further said to include an annular split washer 54 that is depicted in generally in FIG. 2 and that is cooperable with mounting apparatus 62. More particularly, mounting apparatus 62 can be said to have an annular channel 68 formed thereon, and split washer 54 has a radial split 56 formed therein which enables split washer 54 to be received in channel 68, as is depicted generally in FIG. 4. Split washer 54 serves as a brace element that retains frame 14 situated on connector 36.

More specifically, and as can be understood from FIGS. 3 and 4, mounting apparatus 62 further has a ledge 72 formed thereon which, in the exemplary embodiment depicted herein, is of an annular shape. The region of mounting apparatus 62 that extends between channel 68 and ledge 72 is in the form of an annular boss 74. Moreover, frame 14 can be said to include a lip 76 adjacent opening 16, and lip 76 can be said to be the region of frame 14 peripheral to opening 16. When connector 36 is received in opening 16 in frame 14 and split washer 54 is received in channel 68, lip 76 of frame 14 is retained between ledge 72 and split washer 54. Moreover, boss 74 is receivable within opening 16.

It thus can be understood from FIG. 4 that when frame 14 is mounted on connector 36, lip 76 of frame 14 is retained between boss 74, ledge 72, and split washer 54, with split washer 54 serving as a brace element 54 that limits axial movement of frame 14 along an axis 70 of mounting apparatus 62 and connection apparatus 50. In this regard, ledge 72 can likewise be said to function as a brace element to resist such axial movement of frame 14 along axis 70. Boss 74 can be said to limit movement of frame 14 in directions perpendicular to axis 70. It is noted, however, that boss 74, ledge 72, and split washer 54 advantageously do not resist pivotable movement of frame 14 with respect to connector 36 about axis 70, and rather such pivotable movement is permitted. Frame 14 and headgear 8 are thus pivotably mounted on connector 36.

As can be understood from FIG. 3, connection apparatus 50 is disposed on support apparatus 48 adjacent mounting apparatus 62. Connection apparatus 50 can be said to include an engagement element 78 mounted on mounting apparatus 62 and a retention apparatus 80 mounted on engagement element 78 at an end thereof opposite mounting apparatus 62. Engagement element 78 includes an outer engagement surface 84 that is of a substantially frusto-conic configuration. Engagement surface 84 is structured to receive against it seal surface 30 of seal element 28 of cushion 12, it being reiterated that seal surface 30 likewise has a frusto-conic shape. The engagement of engagement surface 84 and seal surface 30 is depicted generally in FIG. 4.

As can further be understood from FIG. 3, retention apparatus 80 includes a plurality of retention elements 86 that that protrude outwardly from engagement surface 84 in a direction generally away from axis 70. Retention elements 86 each include a retention surface 88 that faces in a direction generally toward support apparatus 48. As can be understood from FIG. 4, retention surfaces 88 of retention elements 86 are engaged with abutment surface 32 of seal element 28 when seal surface 30 is received against engagement surface 84. This is the scenario depicted generally in FIG. 4 despite the slight spacing depicted between engagement surface 84 and seal surface 30 which is provided merely for purposes of clarity of disclosure. It can be understood from FIG. 4 that the engagement of retention elements 86 with seal element 28 at abutment surface 32 retains seal element 28 sealingly engaged with engagement element 78 by maintaining the engagement between seal surface 30 and engagement surface 84 in a fashion that is substantially airtight and that resists leaking therethrough of the flow of breathable gases within the range of pressures that are likely to be experienced by patient interface 2.

Retention apparatus 80 retains cushion 12 on engagement element 78 and thus on connector 36 in a fashion that promotes the reliable and leak-resistant provision of the flow of breathable gas to the patient. It is also noted that the retention of seal element 28 between engagement surface 84 and retention surfaces 88 resists axial movement of cushion 12 along axis 70 without resist pivoting movement of cushion 12 about axis 70. Thus, while connection apparatus 50 retains cushion 12 mounted to connector 36, cushion 12 and connector 36 are nevertheless advantageously pivotable about axis 70 with respect to one another.

Further advantageously, cushion 12 can be removed from patient interface 2 by the patient pulling cushion 12 in a direction along axis 70 and generally away from frame 14. In so doing, seal element 28 slides along retention surfaces 88 until it fully clears connection apparatus 50 and can be removed from connector 36. Cushion 12 can then be washed, replaced, etc. as needed by the user. Still further advantageously, when cushion 12 is returned to connector 36, seal element 28 slides over retention elements 86 until seal surface 30 engages engagement surface 84 and retention surfaces 88 engage abutment surface 32, and such engagements occur more or less simultaneously. Such resultant engagement among the aforementioned surfaces provides a desirable tactile and audible feedback that is detectable by the patient and which confirms to the patient that cushion 12 is properly installed on patient interface 2.

Figure 5:
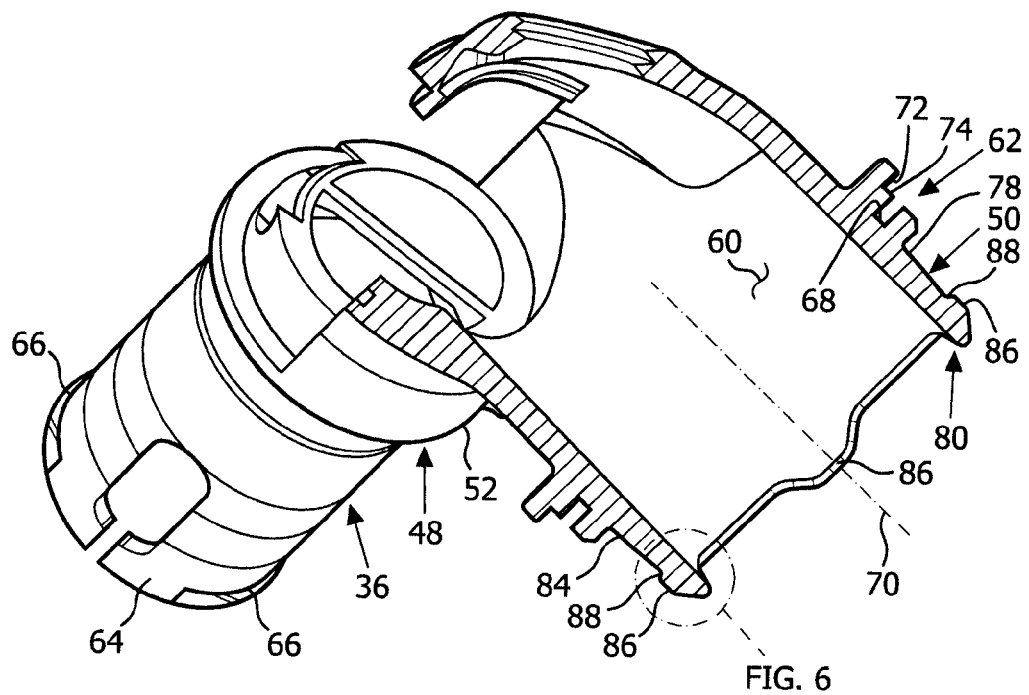
FIG. 5 is a sectional view as taken along line 5-5 of FIG. 3.
Figure 6:
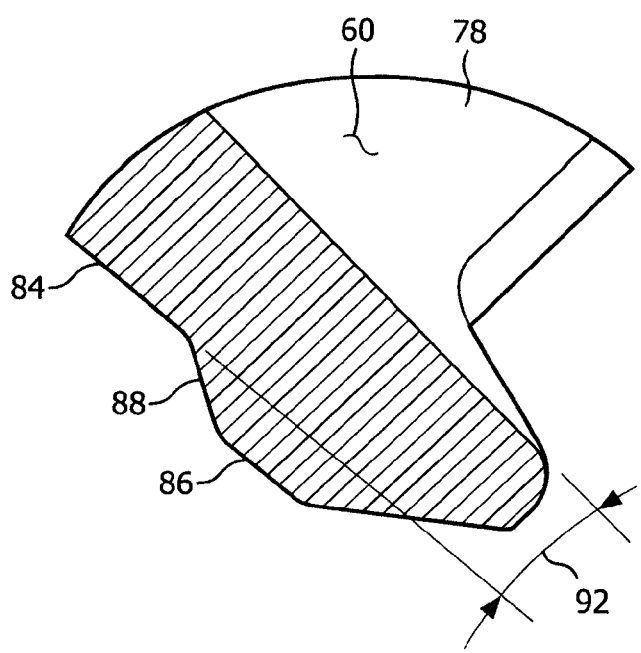
FIG. 6 is an enlarged view of an indicated portion of FIG. 5.

The frusto-conic shape of engagement surface 84 is more expressly depicted in FIG. 5, and it is understood that seal surface 30 is correspondingly shaped in order to sealingly engage engagement surface 84. As can be understood from FIG. 6, engagement surface 84 is oriented at an angle represented generally at the numeral 92 with respect to the inner surface of engagement element 78 adjacent flow passage 60 and thus likewise with respect to axis 70. An angle 92 of approximately five degrees provides a good balance between proving a reliable seal between seal surface 30 and engagement surface 84 while permitting cushion 12 and connector 36 to be pivotable with respect to one another. It is understood that in other embodiments angles greater and lesser than five degrees can be employed without departing from the present concept. Moreover, it is noted that structures similar to those used in connection apparatus 50 for pivotably holding cushion 12 on connector 36, i.e., an engagement element having a frusto-conic engagement surface in combination with a set of retention elements, could also be used in place of mounting apparatus 62 as an alternative system for pivotably mounting frame 14 and thus headgear 8 to connector 36.

It thus can be understood that connector 36 enables headgear 8 and cushion 12 to be pivotable with respect thereto, thus increasing the comfort of patient interface 2, while maintaining a reliable seal between cushion 12 and connector 36. This advantageously increases the reliability with which the flow of breathable gases is provided to the patient. Moreover, cushion 12 is easily removable and replaceable by the patient, and such replacement is accompanied by audible and tactile feedback to the patient, all of which are desirable.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A connector structured to be employed in a patient interface that is structured to provide a flow of breathable gas to an airway of a patient, the patient interface having a resilient cushion that is structured to be engaged with the face of the patient, the connector comprising:
    a support apparatus structured to be connected with a source of breathable gas;

a connection apparatus disposed on the support apparatus and structured to be engaged with the cushion;

the connection apparatus comprising an engagement element and a retention apparatus;

the engagement element having a frusto-conic engagement surface structured to receive against it at least a portion of the cushion; and the retention apparatus comprising at least a first retention element that protrudes outwardly from the frusto-conic engagement surface and that is structured to be engaged with the cushion and to retain the at least portion of the cushion in a condition received against the engagement surface.

2. The connector of claim 1, wherein the at least first retention element is disposed on the engagement element.

3. The connector of claim 1, wherein the retention apparatus comprises a plurality of retention elements spaced apart from one another and disposed about an end of the engagement element opposite the support apparatus.

4. The connector of claim 3, wherein the plurality of retention elements each have a retention surface that faces in a direction generally toward the support apparatus.

5. The connector of claim 1, wherein the patient interface further has a frame structured to be connected with the head of the patient, and wherein the support apparatus comprises a brace element structured to be engaged with the frame.

6. The connector of claim 5, wherein the frame has a substantially circular opening formed therein, and wherein the brace element is substantially annular in shape and is structured to engage the frame in a region peripheral to the opening.

7. The connector of claim 6, wherein the support apparatus has a flow passage formed therein that is structured to deliver the flow of breathable gas, the support apparatus further having an annular channel formed thereon that is structured to receive the brace element therein.

8. The connector of claim 7, wherein the support apparatus further comprises a ledge formed thereon, the ledge and the brace element being structured to retain therebetween the region of the frame peripheral to the opening.

9. The connector of claim 7, wherein the support apparatus further comprises a support element that is elbow-shaped and that has the flow passage formed therein.

10. The connector of claim 7, wherein the support apparatus is structured to be movably connected with both the frame and the cushion.

11. A patient interface comprising the connector of claim 1 and further comprising a resilient cushion that is disposed on the connector and that is structured to be engaged with the face of a patient, the patient interface being structured to provide a flow of breathable gas to an airway of the patient.

12. The patient interface of claim 11, wherein the cushion comprises a seal element having a frusto-conic seal surface that is engageable with the engagement surface, the retention apparatus being engaged with the seal element when the seal surface is engaged with the engagement surface.

13. The patient interface of claim 12, wherein the seal element has an annular abutment surface at an end thereof, the retention apparatus being engaged with the abutment surface when the seal surface is engaged with the engagement surface.

* * * * *